United States Patent [19]

Tuttle

[11] 4,061,142
[45] Dec. 6, 1977

[54] APPARATUS FOR CONTROLLING BLOOD FLOW

[75] Inventor: Glenn L. Tuttle, Bountiful, Utah

[73] Assignee: Sandoz, Inc., E. Hanover, N.J.

[21] Appl. No.: 696,734

[22] Filed: June 16, 1976

[51] Int. Cl.² .............................................. A61M 1/03
[52] U.S. Cl. ..................................... 128/214 R; 251/9
[58] Field of Search ........... 128/214 R, 214 F, 214 E, 128/214.2, DIG. 12, DIG. 13; 137/595, 597; 251/7–9; 210/321

[56] References Cited

U.S. PATENT DOCUMENTS

| 3,543,752 | 12/1970 | Hesse et al. ...................... 128/214 E |
| 3,654,959 | 4/1972 | Kassel ............................... 251/9 X |
| 3,756,234 | 9/1973 | Kopp ................................ 128/214 R |
| 3,918,490 | 11/1975 | Goda ................................. 137/597 |
| 3,985,134 | 10/1976 | Lissot et al. ....................... 128/214 R |
| 3,994,294 | 11/1976 | Knute ............................... 128/214 F |

Primary Examiner—Dalton L. Truluck
Attorney, Agent, or Firm—Gerald D. Sharkin; Robert S. Honor; Walter F. Jewell

[57] ABSTRACT

This invention provides a single needle dialysis blood tubing occluder, comprising in a preferred aspect, a pair of pivotly mounted clamping arms having a leaf spring affixed to the non-pivot end of each occluder with the spring in slidable engagement with a symmetrical cam. Means are provided for actuating the cam, whereby the cam moves the tubing occluder to alternately occlude and non-occlude a pair of blood tubings.

12 Claims, 4 Drawing Figures

APPARATUS FOR CONTROLLING BLOOD FLOW

This invention relates to apparatus for controlling blood flow. More particularly, it relates to the control of blood flow in single needle dialysis.

Single needle dialysis operates on the principle of controlled bi-directional flow of blood through a single lumen bifurcated catheter. Prior art single needle dialysis apparatus control blood flow to and from the patient by alternatively opening and occluding the venous and arterial dialyzer blood tubing lines.

With the increased use of single needle hemodialysis, there there has been a corresponding increase in the use of blood tubing. These blood tubings come in a wide variety of tubing sizes, which has caused much concern in the manufacture of hemodialysis control units in that the equipment must be able to accept all of the different tubing sizes. In the past, this has been accomplished either by sleeves, adaptors, or individual adjustments on the equipment. However, these expedients have not been a satisfactory solution to problems of accommodating a wide variety of tubing sets in the single needle dialysis blood control systems.

Another problem with the prior art single needle dialysis blood control apparatus is the fact that in alternatively opening and occluding the blood tubing, there is a time when both of the blood lines are open, thus creating a problem of admixing of dialyzed and non-dialyzed blood. Also they are noisy, thus providing in addition to the dialysis itself, an additional irritation or trauma to the patient.

It is, therefore, an object of this invention to provide a single needle dialysis blood control apparatus, which is adaptable to accommodate blood tubing sets of various sizes.

It is also an object of this invention to provide a single needle dialysis blood control apparatus which will accommodate blood tubing sets in which the venous and arterial tubing lines are of different sizes.

It is also an object of this invention to provide a single needle dialysis blood control apparatus which does not open both blood lines at the same time; and which is quieter and, therefore, less irritating to the patient.

These and other objects of the invention will become apparent from the following detailed description and drawings, wherein.

Figure 1:
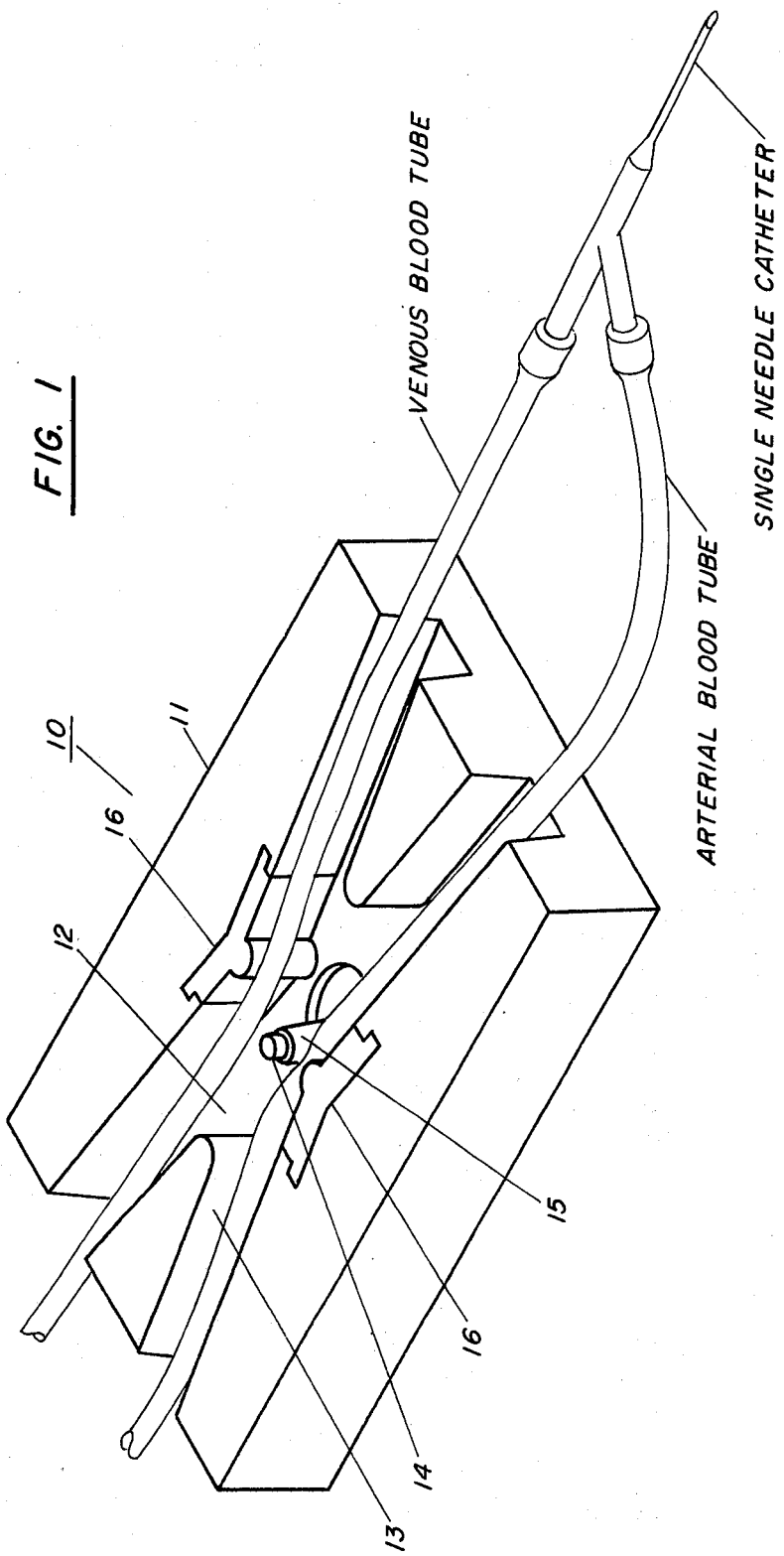
FIG. 1 is an isometric view of a prior art single needle dialysis blood occluder, showing the arterial tubing line occluded.

Broadly, this invention provides an apparatus for controlling blood flow through a pair of blood tubings in a single needle alternating blood flow system. It comprises in combination, a frame, a pair of blood tubing occluders, which are pivotly mounted on the frame, a rotatable cam, which is in slidable engagement with the tubing occluder, and means for actuating the cam. The cam moves the tubing occluders to alternately occlude and non-occlude blood flow through each of the blood tubes.

The cam is preferably symmetrical and generally clam shell-shaped, having a heel portion and a toe portion. It is reversably rotatable through 180° from the apex of the heel portion to the apex of the toe portion. The axis of rotation of the cam is preferably at the intersection of the longitudinal axis and the latitudinal axis of the cam, with the axis through the apex of the heel portion and the toe portion of the cam taken as the longitudinal axis.

In a preferred aspect of the invention, the blood tubing occluder comprises a pair of pivotly mounted clamping arms having a resilient member, e.g., a spring, preferably a leaf spring affixed to the non-pivot end of each occluder, the resilient member being in slidable engagement with the cam at a position tangent to the surface of the cam.

The cam actuation means comprises a reversable motor having a shaft, which is in rotatable communication with the cam. The shaft has on its surface a pair of spaced-apart lobes. A pair of micro-switches are in slidable engagement with the shaft and each switch is in electrical communication with the reversable motor.

The invention further provides that each clamping arm may have an occluder tip on its non-pivoted end, which tip may be situated normal to the horizontal axis of the clamping arm. It is further provided that the occluder tip may be rounded at its blood tubing contacting end. It is also provided that a resilient member, e.g., a spring, preferably a coiled spring, may be between each of the occluder arms and that each end of the resilient members is attached to one of the occluder arms. The purpose of the resilient member being to retract the occluder arms.

There is provided on the frame of the blood tube occluder apparatus a wall portion opposite the occluder tip. A blood tubing is positioned between the wall and the tubing occluder arm, so that when actuated, the occluder arm will press against the tube, squeezing it against the wall to occlude it. It is an additional feature of the apparatus that a clamping pad may be positioned on the wall portion, such that a blood tubing is occluded between the occluder tip and the clamping pad. The clamping pad may be provided with a hemi-cylindrical section projecting toward the occluder tip, against which the blood tubing is occluded.

In an additional embodiment of this invention, the cam actuation means comprises a reversable motor having a shaft in rotatable communication with the cam, a pair of micro-switches, each switch in slidable contact with one end of the cam. The switches are in electrical communication with the reversing motor.

In the operation of the single needle dialysis blood occluder of this invention, a pair of blood tubings are placed along each wall of the frame and one end of each tube is connected to a bifurcated single lumen catheter, and the other ends connected to a hemodialyzer system. As a patient's blood is introduced through the catheter, it flows through the blood tube (the arterial tube) and toward the dialyzer. Simultaneously, the other blood tubing (the venous tube) is occluded to prevent any back flow of blood to the patient. When a sufficient amount of blood has been moved through the dialyzer a signal may be given, for example, by a blood monitoring system, by means of a pressure-time, pressure-pressure, or time-time actuation means to the blood occluder to occlude the arterial line and release the venous line to return the dialyzed blood to the patient.

The blood occluder arms are caused to occlude or non-occlude the blood tubing by means of the cam, which is in communication with the reversable motor. The reversing of the motor alternately causes an occlusion and non-occlusion of each blood tubing.

Specifically, when the resilient member of the tubing occluder is slidably engaged with the apex of the toe portion of the cam, the clamping arm completely occludes a blood tubing. Simultaneously, the resilient member of the other tubing occluder is slidably engaged with the apex of the heel portion of the cam, disengaging the other clamping arm from the other blood tubing and thus non-occluding it.

A complete cycle of the cam is achieved when the cam rotates 180°, stops, and then reverses direction and rotates back 180°. During this cycle, the two clamping arms will be extended and retracted in an alternating clamping sequence.

The motor is actuated by an electrical signal from the pressure-time, pressure-pressure, or time-time actuation means. As the motor turns, one of the two lobes on the shaft makes contact with one of the micro-switches actuating the switch to send an electrical signal to the motor stopping it. In response to another signal from the blood monitoring system, the motor is actuated in the reverse direction, whereupon the other lobe on the shaft makes contact with the other micro-switch actuating the switch to send an electrical signal to the motor again stopping it. This sequence is continuously repeated during the entire dialyzing operation.

It is a feature of this invention that at no time are both the arterial and venous blood lines both non-occluded. In fact, at the point where the cam is causing the clamping arms to change their positions, there is a momentary time when both the arterial and venous blood lines are both occluded.

The resilient member situated between the clamping arms maintains the blood tubing occluder in a state of tension with respect to the cam.

The cam configuration provides for rapid closing of the clamping arm during about the first 75 to 80 percent of clamping arm travel with a deceleration for the final closing of the blood tubing. This allows the blood cells more time to move out of the clamping area, and reduces the amount of hemolysis taking place in the clamping area.

Because of the nature of the occluding mechanism of the invention, it is able to accommodate blood tubings of various sizes. The arterial and venous tubes can be of the same size or different, as the occluding mechanism will adjust to their size. The automatic adjusting of the occluding arm to accommodate the tubing size is brought about by the amount of deflection placed upon the leaf spring as it slidably engages the cam. With the use of a small tube, a small deflection is brought about; and with a large tube, a large deflection is brought about.

This invention will be more easily understood from the following description and a discussion of the invention and a prior art tubing occluder in the single needle dialysis field.

Referring now to FIG. 1, there is shown generally at 10, a prior art single needle dialysis blood tubing occluder. It comprises a frame 11 having tubing channels 12 and 13, a clamping shaft 14, and a pair of clamping pads 16. The apparatus is shown with the arterial line occluded and the venous line non-occluded. In operation, this prior art apparatus in response to a signal from a blood flow monitoring means (not shown) actuates a pair of solenoids (not shown) to move the clamping shaft 14 to occlude either the arterial or venous blood tubings. The clamping shaft 14 can only travel a fixed distance between the clamping pads 16. This then limits the size of the blood tubing which can be accommodated. To accommodate small tubing, which would not necessarily be compressed between the clamping shaft 14 and the clamping pads 16, a sleeve 15 must be placed over the clamping shaft. This prior art apparatus is not able to accommodate mixed tubing sizes; that is, where a large tubing would be used for one blood line and a small tubing would be used for the other blood line.

Additionally, in the cycling of the clamping shaft 14 of the prior art apparatus, there is a point when the clamping shaft 14 is centered so that both blood tubing lines are non-occluded. It should also be noted that if power is cut off to the unit, the clamping shaft 14 will return to its center position leaving both blood tubings non-occluded.

Figure 2:
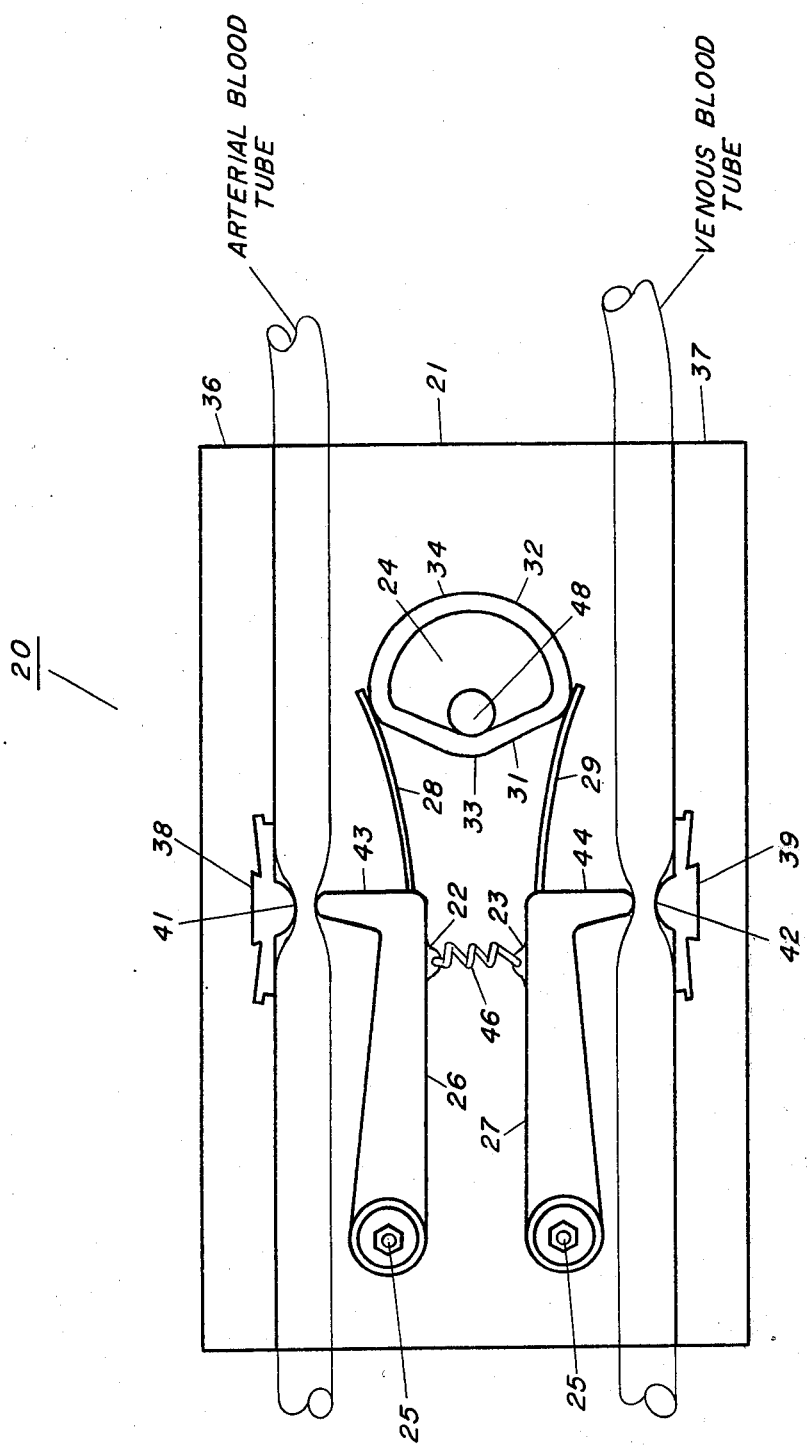
FIG. 2 is a top view of a single needle dialysis blood occluder of this invention, showing different sized blood tubing with both blood tubings occluded.

Referring now to FIG. 2, there is shown generally at 20 a blood tubing occluder apparatus of this invention. It comprises in combination a frame 21, a pair of blood tubing occluders 22 and 23, and a rotatable cam 24. The occluders 22 and 23 are pivotly secured to the frame 21 by conventional fasteners 25. The blood tubing occluders 22 and 23 each consist of a clamping arm 26 and 27, and a resilient member 28 and 29. The resilient members are preferably each a leaf spring. The cam 24 is generally clam shell-shaped having a heel portion 31 and a toe portion 32. The heel portion has its apex at 33 and the toe portion has its apex at 34. The frame has a wall portion 36 and 37 opposite each of the clamping arms 26 and 27. The wall portions 36 and 37 each have a clamping pad 38 and 39, positioned on the wall. These clamping pads are preferably recessed in the wall portion. Each of the clamping pads 38 and 39 are provided with a hemi-cylindrical section 41 and 42 projecting towards the clamping arms 26 and 27.

The clamping arms 26 and 27 are further provided with occluder tips 43 and 44. Preferably, each tip is positioned normal to the horizontal axis of the clamping arm and projects towards the clamping pads 38 and 39, respectively. The occluder tips 43 and 44 preferably each have a rounded tip.

Positioned between the clamping arms 26 and 27 is a resilient member 46, which is preferably a coil spring. This coil spring is affixed at each end to one of the clamping arms 26 and 27 and maintains a bias tension between them.

FIG. 2 also shows a pair of blood lines; that is, an arterial line and a venous line, both of which are shown in an occluded state. It should be noted that the arterial line is of a larger diameter than the venous line.

Figure 3:
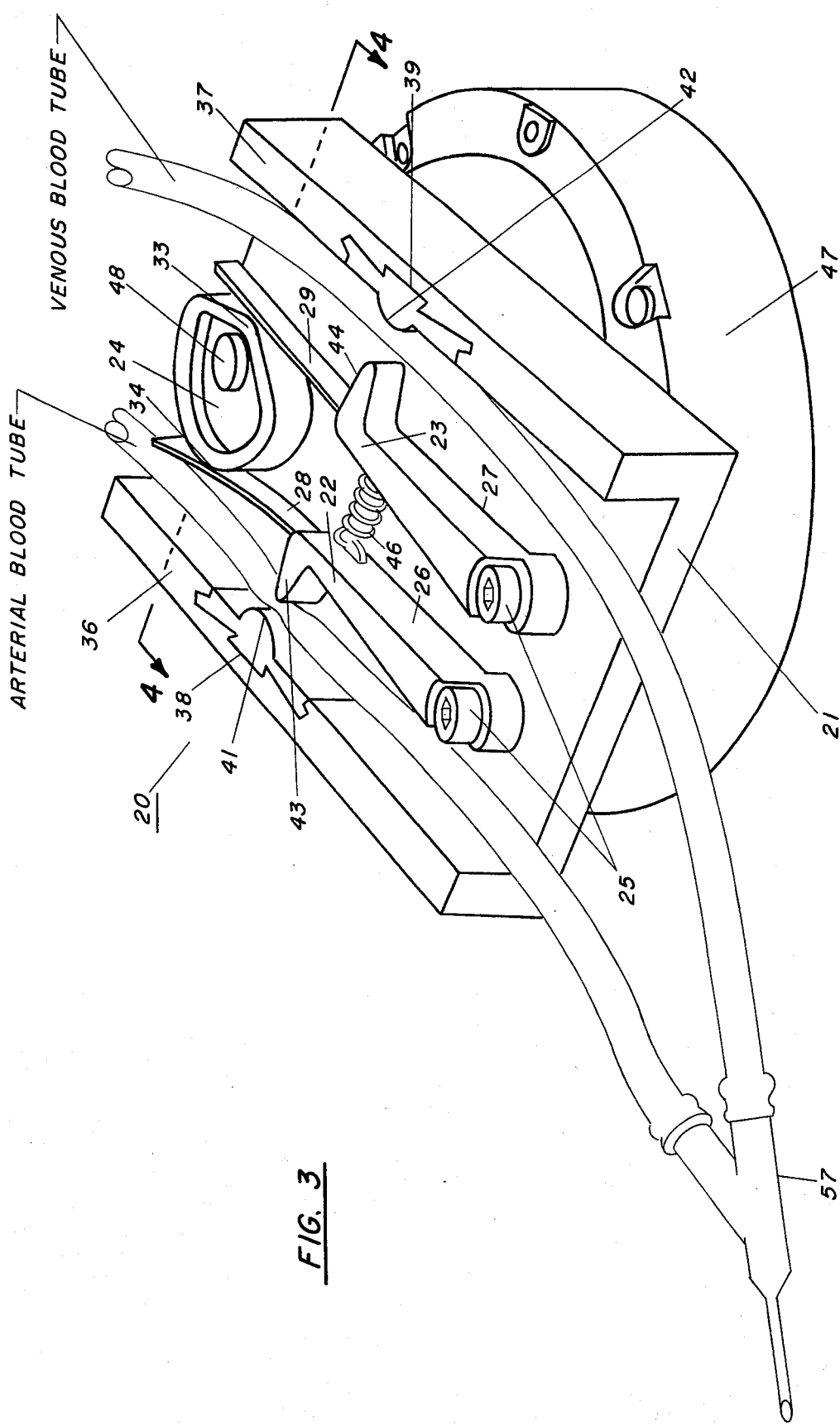
FIG. 3 is an isometric view of the single needle dialysis blood occluder of FIG. 2.

FIG. 3 shows the apparatus 20 of FIG. 2 in isometric detail with a reversable motor 47, positioned below the frame 21. This motor is preferably a D.C. gear-reduced pancake motor, such as that manufactured by the PMC Division of Kollmorgen Corporation, Glen Cove, New York. FIG. 3 also shows the arterial blood line occluded and the venous blood line non-occluded; and it should be noted that both of these lines are of the same diameter.

Figure 4:
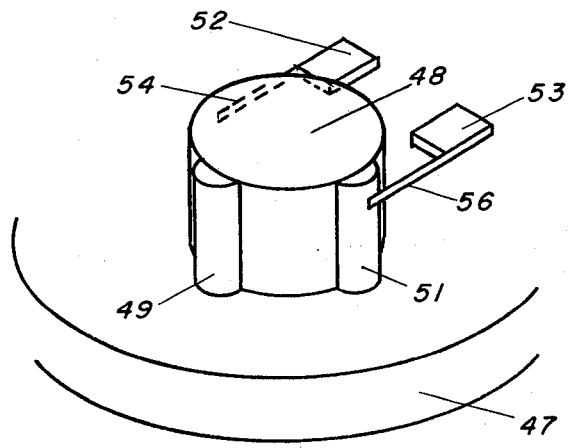
FIG. 4 is an isometric view of the actuating means of the single needle dialysis blood occluder of FIG. 3, along the line 4 — 4.

FIG. 4 shows the area between the motor 47 and the frame 21, wherein a shaft 48, which is in rotatable communication between the motor 47 and the cam 24, has on its surface a pair of spaced-apart lobes 49 and 51. Mounted on the underside of the frame 21 are a pair of Hall-effect micro-switches 52 and 53, which are in slidable contact with the shaft 48 by means of a resilient member 54 and 56. The resilient members 54 and 56 are preferably leaf springs.

In operation, blood is introduced into a single lumen bifurcated catheter 57; and hence into the arterial blood line. At this point, the arterial line is not occluded and the venous line is occluded. When the blood has passed via the arterial blood line through the dialyzer system, a signal is sent from a blood monitoring system (not shown) to the motor 47 actuating it. The motor 47 rotates the cam 24 via shaft 48, causing the tension on deflected leaf spring 28 to be relieved and putting leaf spring 29 under tension. As the cam continues to rotate, increasing tension on the leaf spring 29 causes it to deflect, thus allowing the occluder tip 44 of the occluder arm 27 to engage the venous blood line and occlude it against the clamping pad 39. Simultaneously, as the tension on leaf spring 28 is removed, the clamping arm 26 is released from its occluding position on the arterial blood line, thus allowing blood to flow through the arterial line.

When the cam has rotated 180° in unison with the rotation of the shaft 48, the lobe 51 contacts leaf spring 56 of the micro-switch 53 actuating it to send a signal to the motor stopping its rotation. Upon a signal from the blood monitoring system the motor 47 is again actuated reversing its rotation 180° and allowing lobe 49 to contact leaf spring 54 of the micro-switch 52, which switch is actuated sending an electrical signal to the motor 47 stopping it. This sequence of events is repeated continuously during the dialysis operation allowing blood to alternately flow into the arterial line and from the venous line; and hence to and from the patient.

The blood tubing occluding apparatus of this invention provides an advance in the art of single needle dialysis by diminishing the amount of admixing of dialyzed and non-dialyzed blood; accommodating blood tubings of various sizes without necessitating any change within the apparatus, and providing for a quiet and efficient blood occluding operation.

What is claimed is:

1. An apparatus for controlling blood flow through a pair of blood tubings in a single needle alternating blood flow system, which comprises in combination a support frame, a pair of pivotly mounted clamping arms connected to said frame and mounted parallel to one another, said arms having a leaf spring affixed to the non-pivot end of each clamping arm and extending axially therefrom, a rotatable cam positioned between and in slidable engagement with the leaf springs, and means for actuating the cam, whereby the cam moves the leaf spring-clamping arms to alternately occlude and non-occlude a blood tubing.

2. The apparatus according to claim 1, wherein the cam is symmetrical, and the cam actuation means comprises a reversable motor having a shaft in rotatable communication with the cam, the shaft having a pair of spaced-apart lobes, and a pair of micro-switches, which are in slidable engagement with the shaft and in electrical communication with the motor.

3. The apparatus according to claim 2, wherein each clamping arm has an occluder tip.

4. The apparatus according to claim 3, wherein each occluder tip is on the non-pivoted end of a clamping arm.

5. The apparatus according to claim 4, wherein each occluder tip is situated normal to the horizontal axis of a clamping arm.

6. The apparatus according to claim 5, wherein the occluded tip is rounded at its blood contacting end.

7. The apparatus according to claim 6, wherein a resilient member is situated between each of the occluder arms, each end of the resilient member being attached to one occluder arm.

8. The apparatus according to claim 7, wherein the resilient member is a coiled spring.

9. The apparatus according to claim 8, wherein the frame on each side of the tubing occluder has a wall portion opposite the occluder tip.

10. The apparatus according to claim 9, wherein a clamping pad is positioned on the wall portion.

11. The apparatus according to claim 10, wherein the clamping area of the clamping pad is a hemicylindrical section projecting toward the occluder tip.

12. The apparatus according to claim 1, wherein the cam actuation means comprises a reversable motor having a shaft in rotatable communication with the cam, a pair of micro-switches, each switch in slidable contact with one end of the cam, the switches in electrical communication with the motor.

* * * * *